US00PP22205P2

(12) United States Plant Patent
Zlesak

(10) Patent No.: US PP22,205 P2
(45) Date of Patent: Oct. 25, 2011

(54) SHRUB ROSE PLANT NAMED 'ZLEMARIANNE YOSHIDA'

(50) Latin Name: *Rosa hybrida*
Varietal Denomination: ZLEMarianne Yoshida

(76) Inventor: David Charles Zlesak, St. Paul, MN (US)

( * ) Notice: Subject to any disclaimer, the term of this patent is extended or adjusted under 35 U.S.C. 154(b) by 0 days.

(21) Appl. No.: 12/803,558

(22) Filed: Jun. 30, 2010

(51) Int. Cl.
*A01H 5/00* (2006.01)

(52) U.S. Cl. ..... Plt./107

(58) Field of Classification Search ..... Plt./107
See application file for complete search history.

*Primary Examiner* — Annette Para

(57) ABSTRACT

Shrub rose plant having a mounded, well-branched, compact plant habit; vigorous growth; double flowers typically borne in clusters of 3 or more; peach-pink petal color; continuous flowering throughout the growing season; resistance to major fungal diseases and ability to root and grow vigorously from softwood and semi-hardwood cuttings.

3 Drawing Sheets

Latin name of the plant claimed: *Rosa hybrida.*
Variety denomination: 'ZLEMarianneYoshida'.

BACKGROUND OF THE INVENTION

The primary objective of making this cross was to produce a new rose variety having the vigorous growth habit, continuous blooming habit, attractive flower form, and winter hardiness of the female parent and the disease resistance, and flower color of the male parent. The pollination occurred in late spring 2003. The seed germinated during the winter of 2003/2004 and 'ZLEMarianneYoshida' was identified as a superior seedling and first asexually propagated in 2004.

The present invention relates to a new and distinct variety of rose plant of the shrub commercial class designated 'ZLEMarianneYoshida' which was originated by me by crossing two of my unnamed seedling selections (female parent is seedling selection 1G15 and the male parent is seedling selection 1B30).

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Mounded, well-branched, compact plant habit;
2. Vigorous growth;
3. Double flowers typically borne in clusters of 3 or more;
4. Peach-pink petal color;
5. Continuous flowering throughout the growing season;
6. Resistance to major fungal diseases;
7. Ability to root and grow vigorously from softwood and semi-hardwood cuttings.

Asexual reproduction of this new variety by rooting softwood and semi-hardwood cuttings, as performed at St. Paul, Minn., shows that the foregoing and all other characteristics and distinctions come true to form and are established and transmitted through succeeding propagations.

Comparison with Parents

'ZLEMarianneYoshida' has double peach-pink flowers and a mounded, well-branched, compact habit which differs from the female parent, 1G15, which has double red blooms and a narrow, upright plant habit. 'ZLEMarianneYoshida' differs from the male parent, 1B30, in that 1B30 has non-recurrent flowering (typically 4-6 weeks of flowering in late spring to early summer) and 'ZLEMarianneYoshida' is continuously flowering during the growing season and the plant and flower size of 1 B30 is larger than 'ZLEMarianneYoshida'. 'ZLEMarianneYoshida', 1G15, and 1B30 have all proven to be reliably crown hardy in St. Paul, Minn. (United States Department of Agriculture cold hardiness zone 4).

Comparison with Similar Variety

The rose variety with the greatest similarity to 'ZLEMarianneYoshida' is 'Meiggili' (marketed under the names Peach Drift® and Peach Compact Meidiland®; U.S. Plant Pat. No. 18,542), a rose of the shrub commercial class. Both 'ZLEMarianneYoshida' and 'Meiggili' have double, peach to peach-pink blooms borne in clusters and have a relatively compact plant habit. 'ZLEMarianneYoshida' has blooms that typically are slightly more pink and a plant habit that is taller and less spreading than 'Meiggili'.

BRIEF DESCRIPTION OF THE DRAWINGS

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

Figure 1:
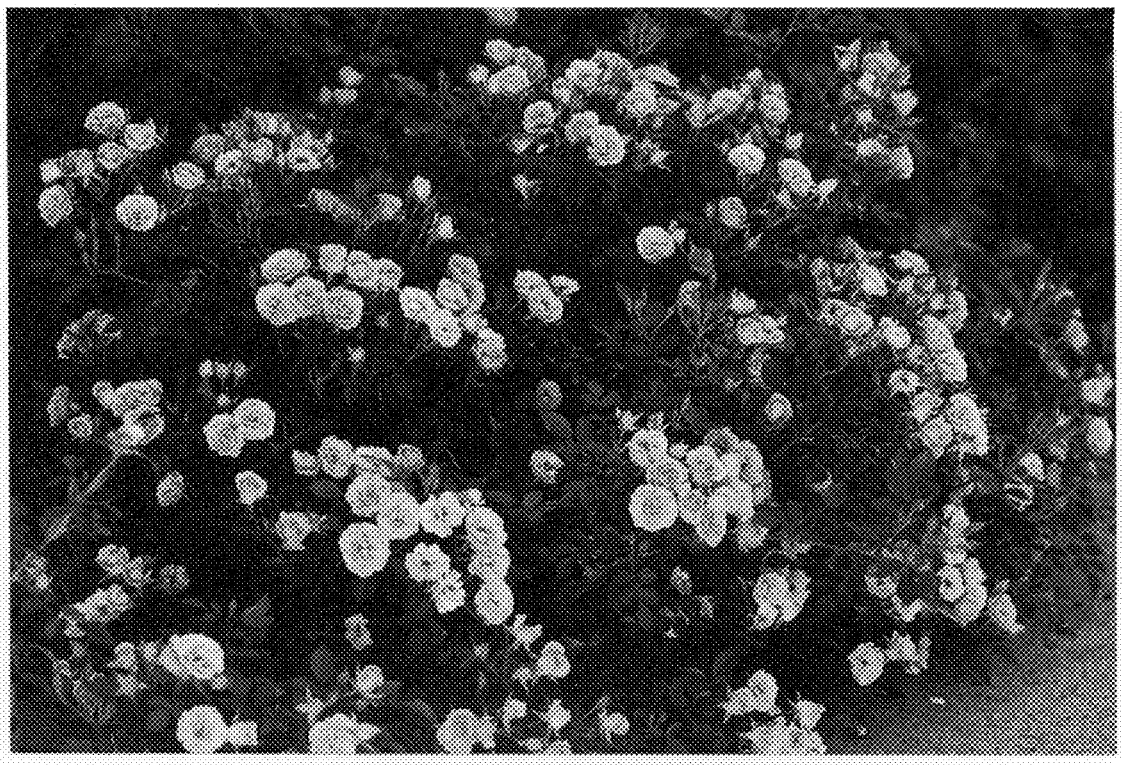
FIG. 1 illustrates a mature plant growing in a landscape during its first cycle of bloom in June.
Figure 2:
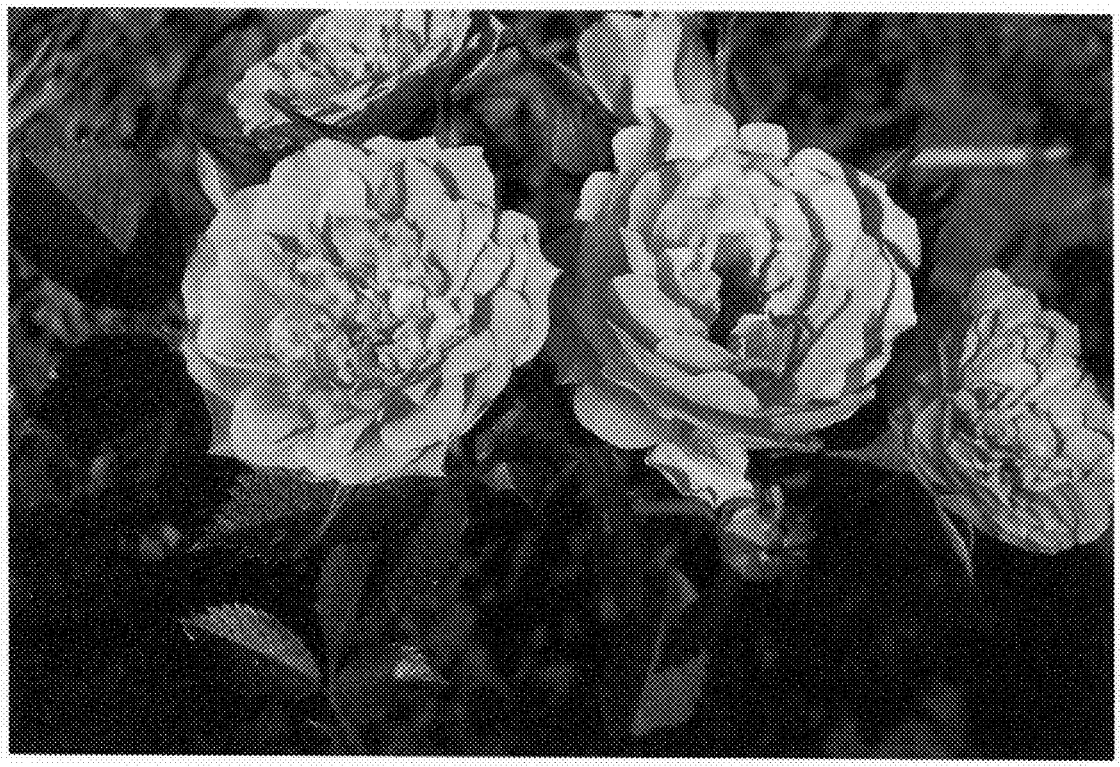
FIG. 2 illustrates a close up view of a group of flowers that are fully opened.
Figure 3:
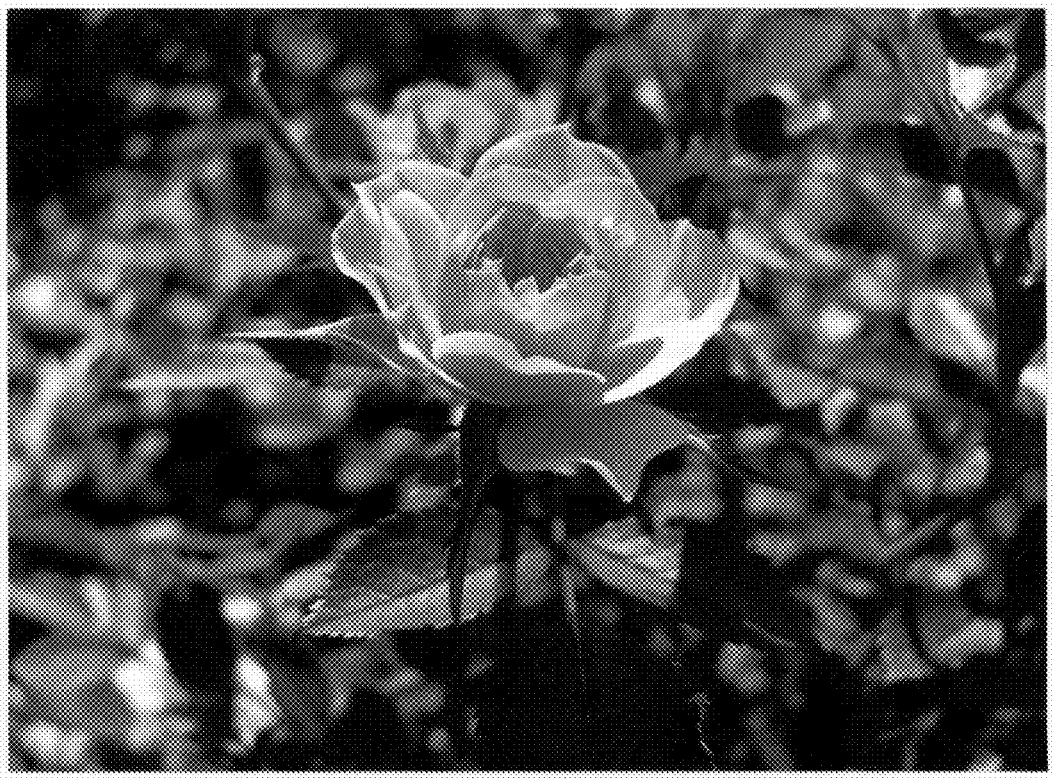
FIG. 3 illustrates a close up view of a flower that is partially opened.
Figure 4:
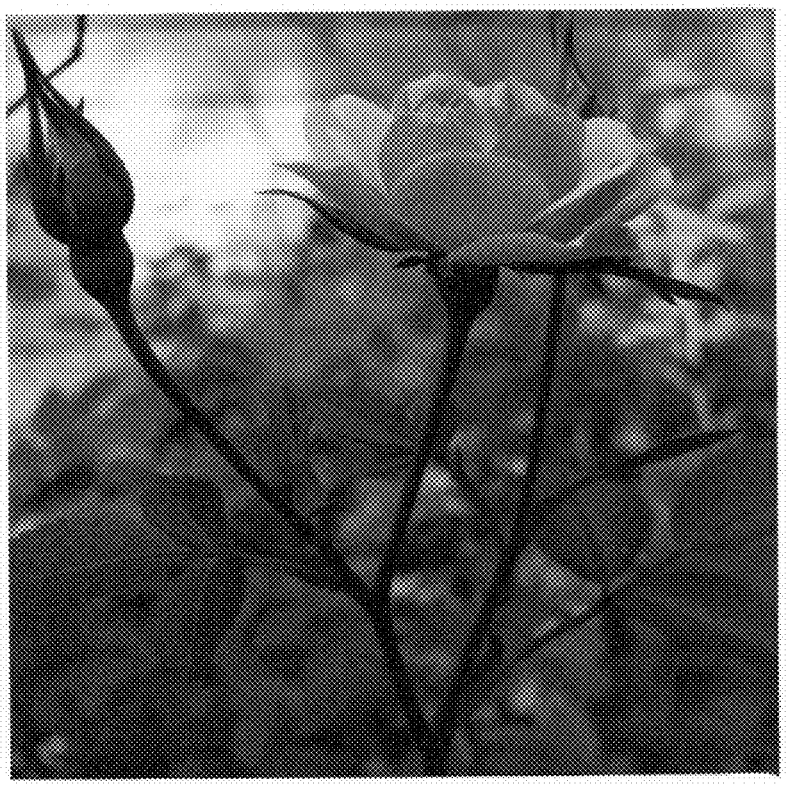
FIG. 4 illustrates a side view of both an unopened flower bud and a partially opened flower.
Figure 5:
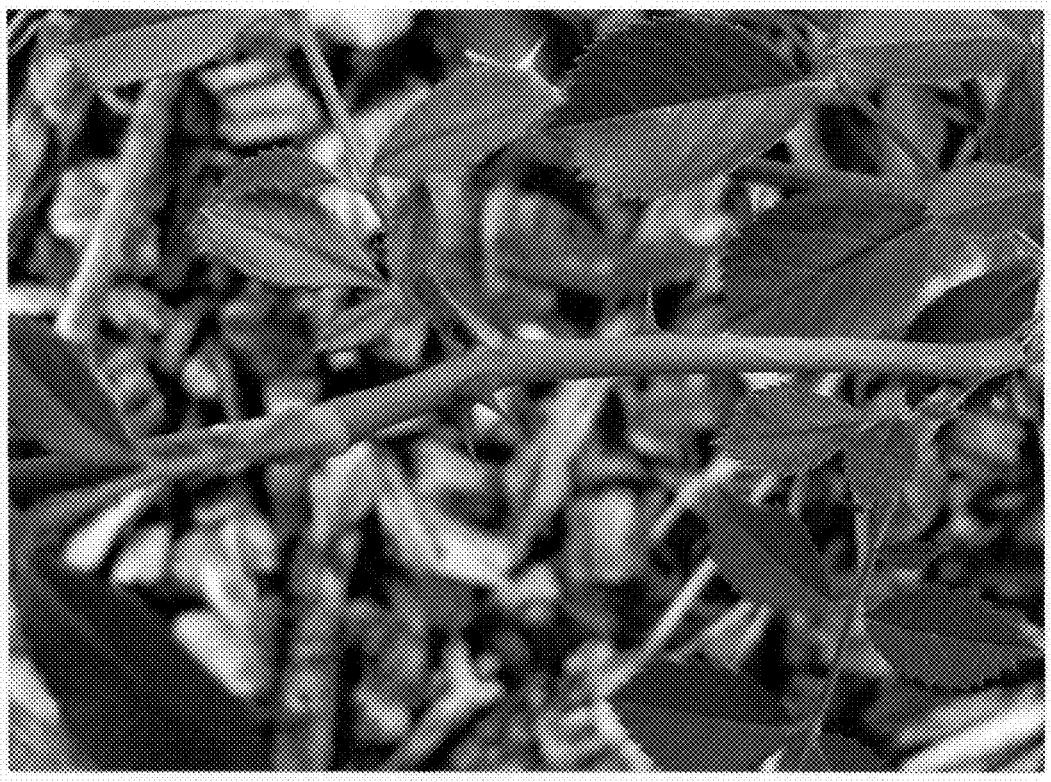
FIG. 5 illustrates prickles on a typical young, flowering stem.
Figure 6:
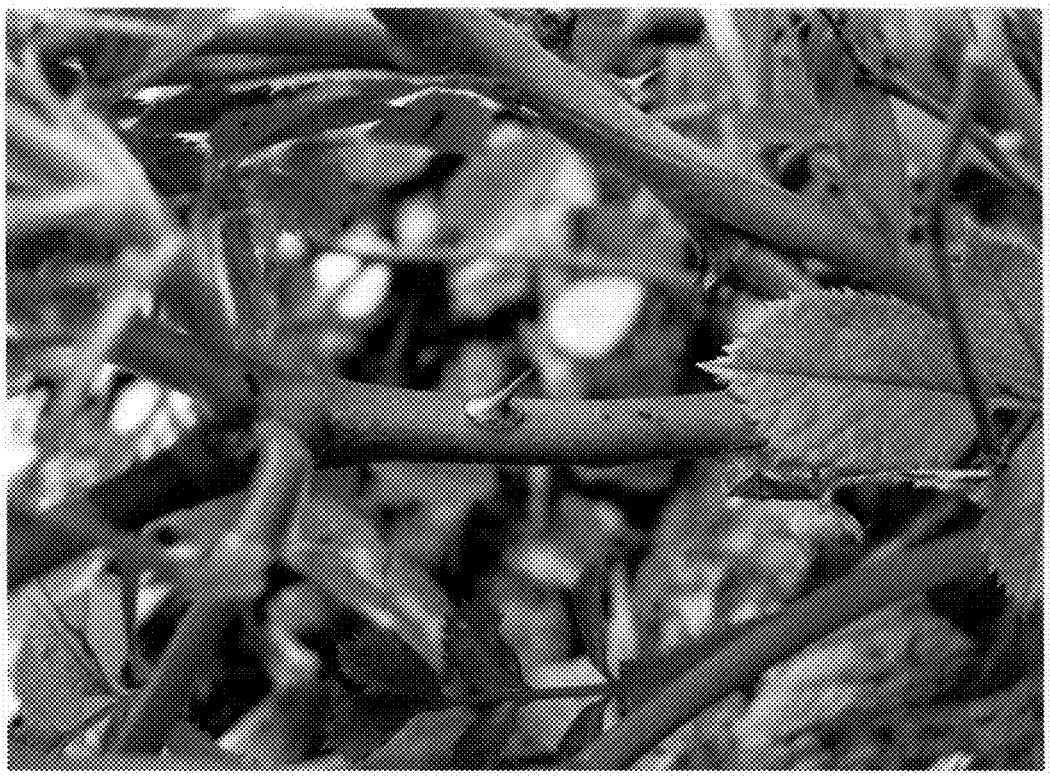
FIG. 6 illustrates prickles on an older stem from the previous growing season with mature coloration.

The following is a detailed description of my new rose cultivar with color descriptions using terminology in accordance with The Royal Horticultural Society (London) Colour Chart (2001), except where ordinary dictionary significance of color is indicated. The phenotype of the new cultivar may vary with variations in environmental, climatic, and cultural conditions, as it has not been tested under all possible environmental conditions. Descriptions are based on observations of plants approximately four years of age that were propagated from semi-hardwood cuttings and are not grafted onto rootstock.

Parentage:

*Seed parent.*—An unnamed seedling never released for sale of the shrub commercial rose class from my breeding program, which I designate as 1G15. The female parent of 1G15 is 'CURlem' (non-patented in the United States) and the male parent of 1G15 is 'George Vancouver' (disclosed in U.S. Plant Pat. No. 10,009).

*Pollen parent.*—An unnamed seedling never released for sale of the shrub commercial rose class from my breeding program, which I designate as 1B30. The female parent of 1B30 is 'Orange Honey' (disclosed in U.S. Plant Pat. No. 4,496) and the male parent is a complex hybrid involving numerous shrub rose cultivars and was never released for sale.

Classification:

*Botanical.*—*Rosa hybrida.*

*Commercial.*—Shrub.

Flower:

Blooming habit: Continuous.

Bud:

*Size.*—16-18 mm long and 10-13 mm in diameter when the petals start to unfurl.

*Form.*—The bud form is ovoid and pointed.

*Color.*—When sepals first divide, visible petal color is Orange Group 25D. When half blown, the upper or adaxial sides of the petals are closest to Red Group 37C on the distal end and Yellow Group 9C at the proximal end. The lower or abaxial sides of the petals are Orange Group 29C at the distal end and Yellow Group 5C at the proximal end.

*Sepals.*—Color: Green Group 137C on the abaxial side and Green Group 138B on the adaxial side. Length: 18-22 mm. Width: 4-5 mm. Shape: ovate to oblong with acuminate tips. Surface texture: Adaxial, Hoary. Abaxial, Generally smooth with some very small glandular hairs. There are three lightly appendaged sepals. There are two unappendaged sepals which have hoary edges.

*Receptacle.*—Color: Green Group 137D. Shape: round to slightly elliptic. Size: Small, about 5 mm wide and 5 mm long. Surface: glabrous.

*Peduncle.*—Length: Medium, averaging about 30-35 mm. Surface: glabrous. Color: Yellow-Green Group 146C. Strength: Stiff, primarily erect.

Bloom:

*Size.*—Small. Typical open diameter is 40-45 mm.

*Borne.*—Typically in clusters of 3 or more blooms per stem.

*Stems.*—Strength: Strong. Length: Typically about 20-30 cm. Stem diameter: Varies and is typically 4-6 mm. Larger stems arising from the base of the plant are about 0.8-1.0 cm in diameter, while smaller stems arising from either the base of the plant or secondary or tertiary stems arising within the plant canopy are typically 3-5 mm in diameter.

*Form.*—When blooms first open: High centered with petals unfurling in a symmetrical manner that is commonly called exhibition form by rose growers and exhibitors. When blooms fully open: Slightly cupped to flat.

*Permanence.*—Blooms retain their form to the end.

*Petalage.*—Double blooms with petals and petaloids typically totaling 50-80.

*Color.*—The adaxial sides of the petals are primarily Red Group 51D throughout most of the petal and Yellow Group 9C at the base or proximal end of the petal. The color of the abaxial side of the petals is primarily Red Group 39D.

*Discoloration.*—The general tonality of the adaxial petal surface of a fully open bloom at the first day through the third day: Red Group 37C. The general tonality of the adaxial petal surface at day eight: between Red Group 55D and Red Group 56A. The abaxial surface of the petal is Orange Group 29C typically for the first three days and then gradually fades to Red Group 56A by day eight.

*Fragrance.*—Slight. Character of fragrance: Damask to spicy.

Petals:

*Texture.*—Thick and satiny to the touch.

*Length.*—1.5-2.0 cm.

*Width.*—The outermost petals of the bloom tend to be wider and are typically 1.8 cm and the innermost petaloids are more narrow and are typically 0.5 cm.

*Shape.*—The outermost petals are obcordate and the shape of the petaloids transitions moving towards the center of the flower to obovate and then finally oblong.

*Margin.*—Entire.

*Apex shape.*—Obcordate and sometimes with a small point in the axis for the outermost petals and rounded for the petals towards the center of the bloom.

*Base shape.*—Rounded for the outermost petals and transitioning to cuneate for the inner petals.

*Form.*—Flat to slightly cupped.

*Arrangement.*—Multiple rows of overlapping petals.

*Petaloids.*—Roses have five true petals (except for *Rosa sericea* which typically has four) and all additional petal-like appendages are botanically petaloids. Petaloids are stamens or in some cases also pistils that develop into petal-like structures. However, petaloids that do not have obvious remnant stamen development are often called petals in common vernacular in U.S. Plant Patents and the popular press. 'ZLEMarianneYoshida', like typical roses, has five true petals, frequently has between 42-72 petaloids that look like a typical petal, and often 3-12 petaloids that have some visible stamen development typically seen as a single anther along one of the edges of a relatively narrow petal-like structure. The petaloids with anthers attached are found at the transition area in the bloom between the most petal-like petaloids and the stamens. Pistils in 'ZLEMarianneYoshida' do not develop into petaloids. The size and color of the attached anthers on petaloids for 'ZLEMarianneYoshida' varies, but typically is the same as what is described later for anthers. Additionally, the color of the petal-like portion of the petaloid is typical for the color of a true petal or a more petal-like petaloid without visible anther development.

*Persistence.*—Petals drop off cleanly before drying.

*Lastingness.*—On the plant: Long (about 8-10 days). As a cut flower: Moderate (about 7 days).

Reproductive parts:

*Stamens.*—Number per flower: 55-85. Anthers — Size: Length before dehiscence: 2 mm, Width before dehiscence: 1.5 mm. Length after dehiscence: 1.0 mm. Width after dehiscence: 0.8-1.0 mm. Color: Before dehiscense: Yellow Orange Group 17B. After dehiscense: Yellow-Orange Group 22A. Arrangement: Regular around styles. Filaments — Size: Length: 4-6 mm. Width: 0.25 mm. Color: Yellow-Orange Group 21A. Pollen — Color: Yellow Orange Group 17B.

*Pistils.*—Number per flower: 30-45. Styles — Color: Red Group 51B. Length: 6-8 mm. Stigmas — Color: White Group 155C. Ovary — Color of immature ovary: White Group 155A.

*Hips.*—The fleshy portion of rose hips is hypanthium tissue and inside that tissue are achenes — individual fruits that develop into a single seeded fruit with a hard paricarp surrounding the embryo. Hips are rarely observed on 'ZLEMarianneYoshida'. For those that are present sepals persist and are present upon ripening. Hypanthium: Color immature: Green Group 146A. Color mature: Yellow-Orange Group 15D. Shape: Generally round. Size: 16-18 mm long and 16-18 mm wide.

*Achenes* (*ripe*).—Color: Yellow Green Group 150D. Shape: Irregular. Size: 4-7 mm. Typically there are 1-3 achenes per hip.

Plant:

*Form.*—Rounded bush.

*Growth.*—Very vigorous, well-branched, and dense.

*Age at maturity.*—3 years.

*Mature plant.*—Height is 60 cm and width is 75 cm.

Leaf:

*Form.*—Leaves typically have five or seven leaflets on a typical leaf.

*Arrangement.*—Leaves are alternately arranged on stems.

*Size.*—Medium (9 cm long and 4 cm wide).

*Quantity.*—Normal.

*Leaflet color.*—New foliage: Adaxial side: Yellow-Green Group 146A Abaxial side: Yellow Green Group 146B. Old foliage: Adaxial side: Green Group 137A. Abaxial side: Green Group 137C.

*Leaflet veination pattern.*—Pinnate reticulate.

*Leaflet veination color.*—The color of the veins is the same or very close to that of the overall leaf blade. New foliage: Adaxial side: Yellow-Green Group 146A Abaxial side: Yellow Green Group 146B. Old foliage: Adaxial side: Green Group 137A. Abaxial side: Green Group 137C.

*Leaflet size.*—Terminal leaflets: Medium (3.0-3.5 cm long and 2.0-2.5 cm wide). Non-terminal leaflets: Medium (2.0-2.5 cm long and 1.2-1.5 cm wide).

*Leaflet shape.*—Ovate.

*Leaflet base shape.*—Obtuse.

*Leaflet apex shape.*—Acute to slightly acuminate.

*Leaflet texture.*—Semi-glossy, rugose. On the adaxial side of leaflets the veins are slightly recessed and on the abaxial side they are slightly elevated relative to the general leaf blade.

*Leaflet edge.*—Serrated with small single serrations.

*Petiole.*—color. — Green Group 138B.

*Petiole rachis.*—Color: Green Group 138B and sometimes with Greyed-Red Group 178C highlights on especially the adaxial side.

*Petiole underside.*—Generally smooth with small prickles. Prickles typically are Greyed-Red Group 178B in color.

*Stipules.*—Short (about 1.0-1.3 cm in length). Color: Yellow-Green Group 146A, edges with several relatively parallel and very narrow appendages (0.3-0.5 mm long and 0.1 mm wide).

*Disease resistance.*—Resistant to powdery mildew, black spot, and rust under normal growing conditions.

*Pest persistence.*—Not observed.

Wood:

*New wood.*—Color: Generally Yellow-Green Group 146C with areas of Greyed-Red Group 178C overlaid especially if grown in high light. Bark: Smooth.

*Old wood.*—Color: Yellow-Green Group 146A. Bark: Smooth.

Typical stem prickles:

*Quantity.*—Relatively few with 2-5 typically on a 15 cm length of stem.

*Form.*—Straight to slightly downward hooked.

*Length.*—5-7 mm.

*Width.*—1.0 mm near stem and narrowing to tip.

*Color when young.*—Greyed-Red Group 178A.

*Color when mature.*—Greyed-Yellow Group 161C.

Small, secondary stem prickles:

*Quantity.*—None.

Cytology:

*Ploidy.*—Triploid (2n=3x=21). Meristematic root tip cells in the stage of metaphase of mitosis were observed to have 21 chromosomes under a light microscope at 400× magnification.

Winter hardiness: Consistently crown hardy to United States Department of Agriculture cold hardiness zone 4.

I claim:

1. A new and distinct variety of rose plant of the shrub class, substantially as herein shown and described, characterized particularly by its mounded, well-branched, compact plant habit; vigorous growth; double flowers typically borne in clusters of 3 or more; peach-pink petal color; continuous flowering throughout the growing season; resistance to major fungal diseases and ability to root and grow vigorously from softwood and semi-hardwood cuttings.

* * * * *